United States Patent
Li et al.

(10) Patent No.: US 12,393,659 B2
(45) Date of Patent: Aug. 19, 2025

(54) DISABLEMENT OF DEVICE AUTHENTICATION BASED ON USER SLEEP STATE

(71) Applicant: LENOVO (SINGAPORE) PTE. LTD., Singapore (SG)

(72) Inventors: Scott Li, Morrisville, NC (US); Igor Stolbikov, Morrisville, NC (US); Nathan Peterson, Morrisville, NC (US); Rafael Rodrigues Machado, Morrisville, NC (US)

(73) Assignee: Lenovo (Singapore) Pte. Ltd., Singapore (SG)

( * ) Notice: Subject to any disclaimer, the term of this patent is extended or adjusted under 35 U.S.C. 154(b) by 175 days.

(21) Appl. No.: 18/448,127

(22) Filed: Aug. 10, 2023

(65) Prior Publication Data
US 2025/0053627 A1    Feb. 13, 2025

(51) Int. Cl.
*G06F 21/32*    (2013.01)
*A61B 5/00*    (2006.01)

(52) U.S. Cl.
CPC ............ *G06F 21/32* (2013.01); *A61B 5/4809* (2013.01)

(58) Field of Classification Search
CPC .................. G06F 21/32; G06F 21/554; G06F 2221/2111; A61B 5/4809
See application file for complete search history.

(56) References Cited

U.S. PATENT DOCUMENTS

| | | | |
|---|---|---|---|
| 2016/0350581 A1* | 12/2016 | Manuel | G06V 40/11 |
| 2018/0157817 A1* | 6/2018 | Gao | G06F 21/35 |
| 2019/0312967 A1* | 10/2019 | Sheng | G06F 21/35 |
| 2019/0392125 A1* | 12/2019 | Lee | H04L 63/105 |
| 2021/0099146 A1* | 4/2021 | Lee | G06T 7/73 |
| 2024/0169045 A1* | 5/2024 | Paul | G06F 21/316 |

* cited by examiner

*Primary Examiner* — Christopher B Robinson
*Assistant Examiner* — Tania M Pena-Santana
(74) *Attorney, Agent, or Firm* — John M. Rogitz; John L. Rogitz

(57) ABSTRACT

In one aspect, an apparatus includes a processor assembly and storage accessible to the processor assembly. The storage includes instructions executable by the processor assembly to receive input from at least one sensor on a first device and to determine, based on the input, that a user is asleep. The instructions are also executable to, based on the determination, disable at least a first type of authentication usable to unlock a second device.

20 Claims, 5 Drawing Sheets

DISABLEMENT OF DEVICE AUTHENTICATION BASED ON USER SLEEP STATE

FIELD

The disclosure below relates to technically inventive, non-routine solutions that are necessarily rooted in computer technology and that produce concrete technical improvements. In particular, the disclosure below relates to disablement of device authentication based on user sleep state.

BACKGROUND

As recognized herein, certain types of device authentication are more susceptible to abuse than others. This in turn can lead to digital security issues and other problems.

SUMMARY

Accordingly, in one aspect an apparatus includes a processor assembly and storage accessible to the processor assembly. The storage includes instructions executable by the processor assembly to receive input from at least one sensor on a first device and to determine, based on the input, that a user is asleep. The instructions are also executable to, based on the determination, disable at least a first type of authentication usable to unlock a second device.

Thus, in certain example implementations, based on the determination the instructions may be executable to disable all types of biometric authentication usable to unlock the second device, or even disable any and all types of authentication usable to unlock the second device.

Also in certain example implementations, the first type of authentication may include facial identification, fingerprint identification, and/or other types of biometric authentication.

In various example implementations, the apparatus may include the at least one sensor, the second device, and/or the first device. The second device may therefore be different from the first device. And as a specific example, the first device may include a wearable device, with the wearable device itself including the at least one sensor.

Additionally, in certain example embodiments the input may be first input and the instructions may be executable to receive second input from the at least one sensor, where the second input may be generated later in time than the first input. Here the instructions may then be executable to determine, based on the second input, that the user is awake and to enable the first type of authentication for use to unlock the second device based on the determination that the user is awake.

In various examples, unlocking the second device may include unlocking a lock screen of the second device to access additional applications and features of the second device beyond the lock screen itself.

In another aspect, a method includes receiving input from at least one sensor on a first device and determining, based on the input, that a user is asleep. The method also includes, based on the determination, disabling at least a first type of authentication usable to unlock a second device.

In certain examples, the method may include identifying a wake up signal to wake up the second device from a device inactive state and, based on the determination, declining to wake up the second device from the device inactive state responsive to identification of the wake up signal. The device inactive state may include a sleep state and/or a hibernation state.

Also in certain examples, the input may be first input and the method may include, while the user is asleep, receiving second input from a motion sensor on the second device. The second input may indicate movement of the second device. The method may then include, based on the second input, activating a microphone on the second device and/or a camera on the second device.

In still another aspect, an apparatus includes at least one computer readable storage medium (CRSM) that is not a transitory signal. The at least one CRSM includes instructions executable by a processor assembly to receive input from at least one sensor and to determine, based on the input, that a user is asleep. The instructions are also executable to, based on the determination, disable at least a first type of authentication executable by a device.

In certain example embodiments, the instructions may be executable to identify a wake up signal to wake up the device from a device inactive state. The instructions may also be executable to, based on the determination, decline to wake up the device from the device inactive state responsive to identification of the wake up signal.

Also in certain examples, the input may be first input and the instructions may be executable to, while the user is asleep, receive second input from a motion sensor. The second input may indicate movement of the device. Based on the second input, the instructions may then be executable to activate a microphone on the second device and/or a camera on the second device. In some cases, the device may be a first device and the instructions may be executable to, based on the second input, activate both the microphone and the camera and then to, based on the activation, stream third input from the microphone and fourth input from the camera to a second device different from the first device.

Also in various example embodiments, the apparatus may include the processor assembly.

The details of present principles, both as to their structure and operation, can best be understood in reference to the accompanying drawings, in which like reference numerals refer to like parts, and in which:

DETAILED DESCRIPTION

Figure 1:
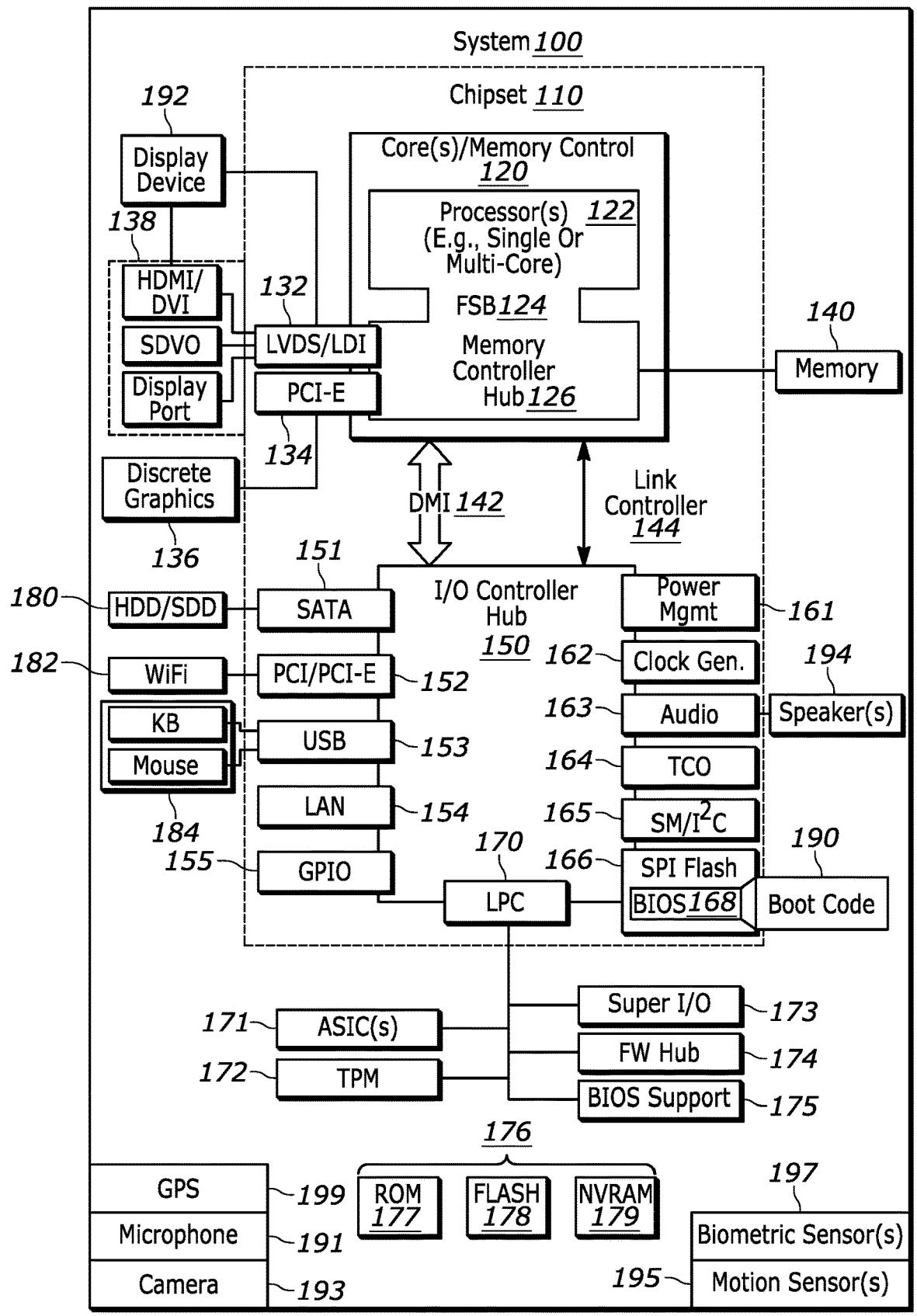
FIG. 1 is a block diagram of an example system consistent with present principles.

Among other things, the detailed description below deals with various forms of authentication that may be enabled and disabled based on a designated device user being determined to be awake or asleep, respectively. As such, forms of authentication encompassed by present principles include biometric authentication (e.g., fingerprint authentication facial recognition, eye/iris recognition), pin/password entry, touch display swipe patterns, and others. The designated user may be the owner of the device, an end-user that has registered his/her biometrics with the device for biometric authentication to the device, an end-user for which sleep is being actively electronically monitored for enabling/disabling device authentication consistent with present principles, etc.

The detailed description below also recognizes that biometric forms of authentication in particular can be prone to abuse while the designated user is sleeping, whether at home or in a public place. For example, a nefarious actor might use the user's finger or face to unlock the user's phone via fingerprint/facial recognition when the user is sound asleep, permitting that nefarious actor to then extract sensitive information from the phone and take other harmful digital actions.

With the foregoing in mind, different sleep tracking devices and methods may be used consistent with present principles. These include electroencephalogram (EEG) headbands, IFTTT sleep applets, and other means to track whether a user is asleep. Wrist wearables with biometric sensors and other types of devices may also be used for sleep/wake cycle detection.

Accordingly, in various examples, when a device has multiple authentication methods, the device may query a paired wearable device to determine the user's wake/sleep state over a secure channel (e.g., encrypted wireless channel and/or paired Bluetooth link). If the user is determined to be in a sleep state, then certain relatively vulnerable authentication methods based on this context (like biometric authentication) may be disabled.

Additionally, in some examples, based on user preference, all authentication methods may be locked/disabled when the user is determined to be in a sleep state.

What's more, a device's power cycle behavior can be altered based on the user's sleep state. For example, the device may remain in a sleep state when the user is asleep, even if there's wake events that are detected.

Still further, a device sensor trigger can be set based on the user sleep state. For example, while the user is in a sleep state, motion at the device's accelerometer can be set as trigger for when device is moved, and in response to movement detection a microphone and camera on that device can be switched on as anti-theft countermeasure.

Prior to delving further into the details of the instant techniques, note with respect to any computer systems discussed herein that a system may include server and client components, connected over a network such that data may be exchanged between the client and server components. The client components may include one or more computing devices including televisions (e.g., smart TVs, Internet-enabled TVs), computers such as desktops, laptops and tablet computers, so-called convertible devices (e.g., having a tablet configuration and laptop configuration), and other mobile devices including smart phones. These client devices may employ, as non-limiting examples, operating systems from Apple Inc. of Cupertino CA, Google Inc. of Mountain View, CA, or Microsoft Corp. of Redmond, WA. A Unix® or similar such as Linux® operating system may be used, as may a Chrome or Android or Windows or macOS operating system. These operating systems can execute one or more browsers such as a browser made by Microsoft or Google or Mozilla or another browser program that can access web pages and applications hosted by Internet servers over a network such as the Internet, a local intranet, or a virtual private network.

As used herein, instructions refer to computer-implemented steps for processing information in the system. Instructions can be implemented in software, firmware or hardware, or combinations thereof and include any type of programmed step undertaken by components of the system; hence, illustrative components, blocks, modules, circuits, and steps are sometimes set forth in terms of their functionality.

A processor may be any single- or multi-chip processor that can execute logic by means of various lines such as address lines, data lines, and control lines and registers and shift registers. Moreover, any logical blocks, modules, and circuits described herein can be implemented or performed with a system processor, a digital signal processor (DSP), a field programmable gate array (FPGA) or other programmable logic device such as an application specific integrated circuit (ASIC), discrete gate or transistor logic, discrete hardware components, or any combination thereof designed to perform the functions described herein. A processor can also be implemented by a controller or state machine or a combination of computing devices. Thus, the methods herein may be implemented as software instructions executed by a processor, suitably configured application specific integrated circuits (ASIC) or field programmable gate array (FPGA) modules, or any other convenient manner as would be appreciated by those skilled in those art. Where employed, the software instructions may also be embodied in a non-transitory device that is being vended and/or provided, and that is not a transitory, propagating signal and/or a signal per se. For instance, the non-transitory device may be or include a hard disk drive, solid state drive, or CD ROM. Flash drives may also be used for storing the instructions. Additionally, the software code instructions may also be downloaded over the Internet (e.g., as part of an application ("app") or software file). Accordingly, it is to be understood that although a software application for undertaking present principles may be vended with a device such as the system 100 described below, such an application may also be downloaded from a server to a device over a network such as the Internet. An application can also run on a server and associated presentations may be displayed through a browser (and/or through a dedicated companion app) on a client device in communication with the server.

Software modules and/or applications described by way of flow charts and/or user interfaces herein can include various sub-routines, procedures, etc. Without limiting the disclosure, logic stated to be executed by a particular module can be redistributed to other software modules and/or combined together in a single module and/or made available in a shareable library. Also, the user interfaces (UI)/graphical UIs described herein may be consolidated and/or expanded, and UI elements may be mixed and matched between UIs.

Logic when implemented in software, can be written in an appropriate language such as but not limited to hypertext markup language (HTML)-5, Java®/JavaScript, C# or C++, and can be stored on or transmitted from a computer-readable storage medium such as a hard disk drive (HDD) or solid state drive (SSD), a random access memory (RAM), read-only memory (ROM), electrically erasable programmable read-only memory (EEPROM), a hard disk drive or solid state drive, compact disk read-only memory (CD-ROM) or other optical disk storage such as digital versatile disc (DVD), magnetic disk storage or other magnetic storage devices including removable thumb drives, etc.

In an example, a processor can access information over its input lines from data storage, such as the computer readable storage medium, and/or the processor can access information wirelessly from an Internet server by activating a wireless transceiver to send and receive data. Data typically is converted from analog signals to digital by circuitry between the antenna and the registers of the processor when being received and from digital to analog when being transmitted. The processor then processes the data through its shift registers to output calculated data on output lines, for presentation of the calculated data on the device.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

The term "circuit" or "circuitry" may be used in the summary, description, and/or claims. As is well known in the art, the term "circuitry" includes all levels of available integration, e.g., from discrete logic circuits to the highest level of circuit integration such as VLSI, and includes programmable logic components programmed to perform the functions of an embodiment as well as processors (e.g., special-purpose processors) programmed with instructions to perform those functions.

Now specifically in reference to FIG. 1, an example block diagram of an information handling system and/or computer system 100 is shown that is understood to have a housing for the components described below. Note that in some embodiments the system 100 may be a desktop computer system, such as one of the ThinkCentre® or ThinkPad® series of personal computers sold by Lenovo (US) Inc. of Morrisville, NC, or a workstation computer, such as the ThinkStation®, which are sold by Lenovo (US) Inc. of Morrisville, NC; however, as apparent from the description herein, a client device, a server or other machine in accordance with present principles may include other features or only some of the features of the system 100. Also, the system 100 may be, e.g., a game console such as XBOX®, and/or the system 100 may include a mobile communication device such as a mobile telephone, notebook computer, and/or other portable computerized device.

As shown in FIG. 1, the system 100 may include a so-called chipset 110. A chipset refers to a group of integrated circuits, or chips, that are designed to work together. Chipsets are usually marketed as a single product (e.g., consider chipsets marketed under the brands INTEL®, AMD®, etc.).

In the example of FIG. 1, the chipset 110 has a particular architecture, which may vary to some extent depending on brand or manufacturer. The architecture of the chipset 110 includes a core and memory control group 120 and an I/O controller hub 150 that exchange information (e.g., data, signals, commands, etc.) via, for example, a direct management interface or direct media interface (DMI) 142 or a link controller 144. In the example of FIG. 1, the DMI 142 is a chip-to-chip interface (sometimes referred to as being a link between a "northbridge" and a "southbridge").

The core and memory control group 120 includes a processor assembly 122 (e.g., one or more single core or multi-core processors, etc.) and a memory controller hub 126 that exchange information via a front side bus (FSB) 124. A processor assembly such as the assembly 122 may therefore include one or more processors acting independently or in concert with each other to execute an algorithm, whether those processors are in one device or more than one device. Additionally, as described herein, various components of the core and memory control group 120 may be integrated onto a single processor die, for example, to make a chip that supplants the "northbridge" style architecture.

The memory controller hub 126 interfaces with memory 140. For example, the memory controller hub 126 may provide support for DDR SDRAM memory (e.g., DDR, DDR2, DDR3, etc.). In general, the memory 140 is a type of random-access memory (RAM). It is often referred to as "system memory."

The memory controller hub 126 can further include a low-voltage differential signaling interface (LVDS) 132. The LVDS 132 may be a so-called LVDS Display Interface (LDI) for support of a display device 192 (e.g., a CRT, a flat panel, a projector, a touch-enabled light emitting diode (LED) display or other video display, etc.). A block 138 includes some examples of technologies that may be supported via the LVDS interface 132 (e.g., serial digital video, HDMI/DVI, display port). The memory controller hub 126 also includes one or more PCI-express interfaces (PCI-E) 134, for example, for support of discrete graphics 136. Discrete graphics using a PCI-E interface has become an alternative approach to an accelerated graphics port (AGP). For example, the memory controller hub 126 may include a 16-lane (×16) PCI-E port for an external PCI-E-based graphics card (including, e.g., one or more GPUs). An example system may include AGP or PCI-E for support of graphics.

In examples in which it is used, the I/O hub controller 150 can include a variety of interfaces. The example of FIG. 1 includes a SATA interface 151, one or more PCI-E interfaces 152 (optionally one or more legacy PCI interfaces), one or more universal serial bus (USB) interfaces 153, a local area network (LAN) interface 154 (more generally a network interface for communication over at least one network such as the Internet, a WAN, a LAN, a Bluetooth network using Bluetooth 5.0 communication, etc. under direction of the processor(s) 122), a general purpose I/O interface (GPIO) 155, a low-pin count (LPC) interface 170, a power management interface 161, a clock generator interface 162, an audio interface 163 (e.g., for speakers 194 to output audio), a total cost of operation (TCO) interface 164, a system management bus interface (e.g., a multi-master serial computer bus interface) 165, and a serial peripheral flash memory/controller interface (SPI Flash) 166, which, in the example of FIG. 1, includes basic input/output system (BIOS) 168 and boot code 190. With respect to network connections, the I/O hub controller 150 may include integrated gigabit Ethernet controller lines multiplexed with a PCI-E interface port. Other network features may operate independent of a PCI-E interface. Example network connections include Wi-Fi as well as wide-area networks (WANs) such as 4G and 5G cellular networks.

The interfaces of the I/O hub controller 150 may provide for communication with various devices, networks, etc. For example, where used, the SATA interface 151 and/or PCI-E interface 152 provide for reading, writing or reading and writing information on one or more drives 180 such as HDDs, SSDs or a combination thereof, but in any case the drives 180 are understood to be, e.g., tangible computer readable storage mediums that are not transitory, propagating signals. The I/O hub controller 150 may also include an advanced host controller interface (AHCI) to support one or more drives 180. The PCI-E interface 152 allows for wireless connections 182 to devices, networks, etc. The USB interface 153 provides for input devices 184 such as keyboards (KB), mice and various other devices (e.g., cameras, phones, storage, media players, etc.).

In the example of FIG. 1, the LPC interface 170 provides for use of one or more ASICs 171, a trusted platform module (TPM) 172, a super I/O 173, a firmware hub 174, BIOS support 175 as well as various types of memory 176 such as ROM 177, Flash 178, and non-volatile RAM (NVRAM) 179. With respect to the TPM 172, this module may be in the form of a chip that can be used to authenticate software and hardware devices. For example, a TPM may be capable of performing platform authentication and may be used to verify that a system seeking access is the expected system.

The system 100, upon power on, may be configured to execute boot code 190 for the BIOS 168, as stored within the SPI Flash 166, and thereafter processes data under the control of one or more operating systems and application software (e.g., stored in system memory 140). An operating system may be stored in any of a variety of locations and accessed, for example, according to instructions of the BIOS 168.

Still further, the system 100 may include an audio receiver/microphone 191 that provides input from the microphone to the processor assembly 122 based on audio that is detected, such as audio detected at/near a device to which authentication is sought when its user is asleep consistent with present principles. The system 100 may also include a camera 193 that gathers one or more images and provides the images and related input to the processor assembly 122, which might also be done when device authentication is sought while the user is asleep consistent with present principles. The camera may be a digital camera (e.g., with a single image sensor), a three-hundred sixty (360) degree camera with multiple image sensors, a thermal imaging camera, an infrared (IR) camera, a webcam, a three-dimensional (3D) camera, and/or another type of camera otherwise integrated into the system 100 and controllable by the processor assembly 122 to gather still images and/or livestream video consistent with present principles.

Additionally, the system may also include one or more motion sensors 195. The motion sensors 195 may help establish an inertial measurement unit (IMU) in some examples. The motion sensors 195 may include a gyroscope that senses and/or measures the orientation of the system 100 and provides related input to the processor assembly 122, an accelerometer that senses acceleration and/or movement of the system 100 and provides related input to the processor assembly 122, and/or a magnetometer that senses and/or measures directional movement of the system 100 and provides related input to the assembly processor 122.

As also shown in FIG. 1, the system 100 may include one or more biometric sensors 197. The biometric sensors 197 may include a camera, a microphone, a motion sensor, an electroencephalograph, a galvanic skin response sensor, a skin temperature sensor, a heart rate sensor, and/or other types of biometric sensors including additional types of sensors through which a user's sleep state may be monitored consistent with present principles.

Also, the system 100 may include a global positioning system (GPS) transceiver 199 that is configured to communicate with satellites to receive/identify geographic position information and provide the geographic position information to the processor assembly 122. However, it is to be understood that another suitable position receiver other than a GPS receiver may be used in accordance with present principles to determine movement and/or location of the system 100.

It is to be understood that an example client device or other machine/computer may include fewer or more features than shown on the system 100 of FIG. 1. In any case, it is to be understood at least based on the foregoing that the system 100 is configured to undertake present principles.

Figure 2:
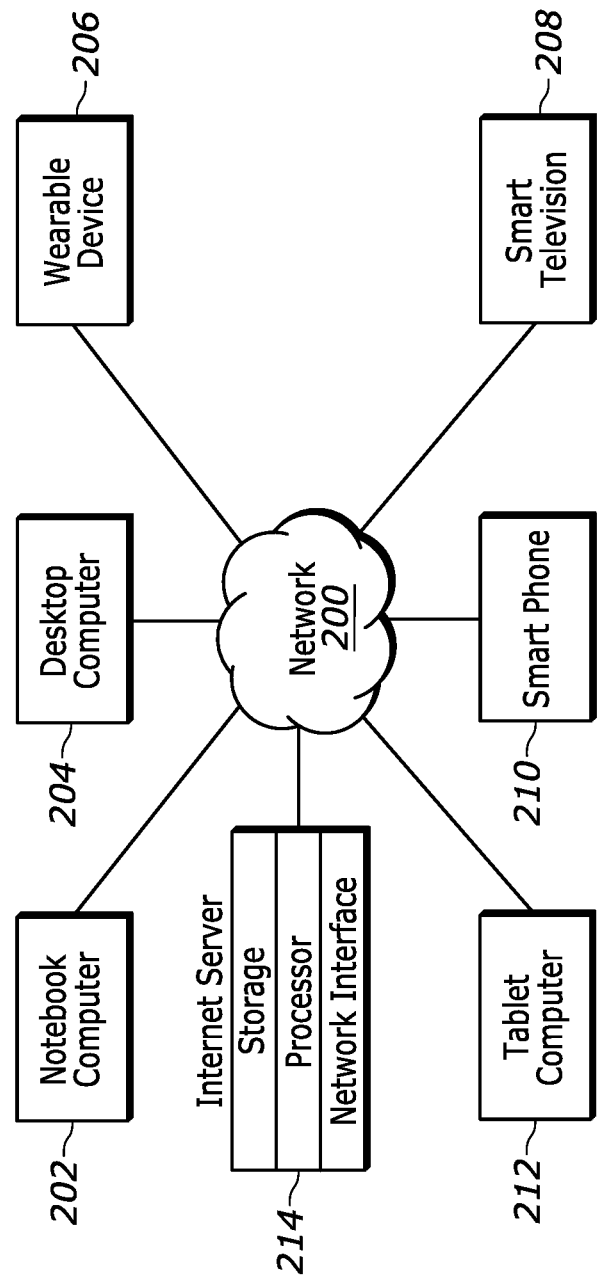
FIG. 2 is a block diagram of an example network of devices consistent with present principles.

Turning now to FIG. 2, example devices are shown communicating over a network 200 such as the Internet, a Bluetooth network, an ultrawideband network, a wireless 5G network, etc. The devices may be communicating to exchange biometric sensor input and to locally/remotely enable and disable various forms of authentication consistent with present principles. It is to be understood that each of the devices described in reference to FIG. 2 may include at least some of the features, components, and/or elements of the system 100 described above. Indeed, any of the devices disclosed herein may include at least some of the features, components, and/or elements of the system 100 described above.

FIG. 2 shows a notebook computer and/or convertible computer 202, a desktop computer 204, a wearable device 206 such as a smart watch or smart glasses, a smart television (TV) 208, a smart phone 210, a tablet computer 212, and a server 214 such as an Internet server that may provide cloud storage accessible to the devices 202-212. It is to be understood that the devices 202-214 may be configured to communicate with each other over the network 200 to undertake present principles.

For example, the devices 202-212 might communicate with each other via paired Bluetooth communication, where one paired device is able to remotely control the functions of the other paired device. Wi-Fi, 5G network, and other Internet-based communications may also be used, as may ultrawideband communication and other types.

Further note that the wearable device 206 itself may be a headband or other type of headset (e.g., smart glasses, augmented/virtual reality headset, headphones or single ear piece, etc.). Additionally or alternatively, the wearable device 206 may be a smart watch, an implantable skin device, or another type of wearable device. Note even further that the wearable device 206 may include one or more of the biometric sensors 197 described above to sense determine whether a user is awake or asleep consistent with present principles.

Figure 3:
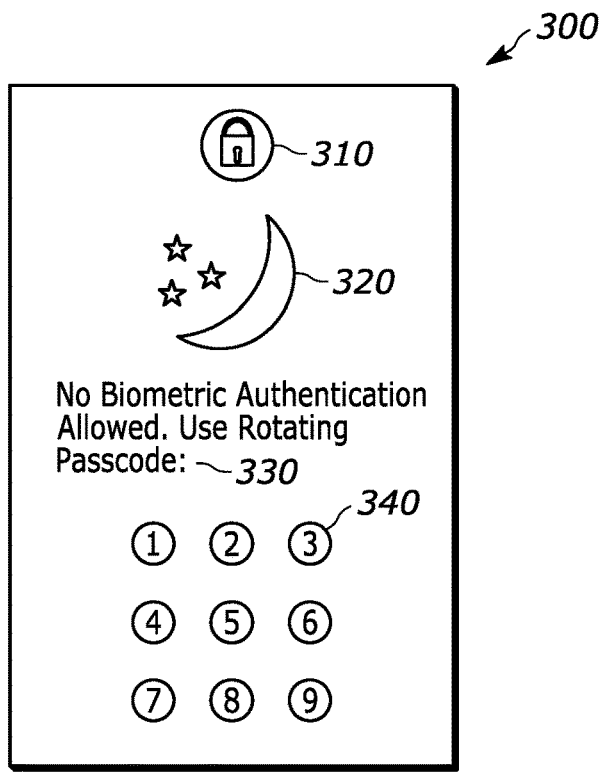
FIG. 3 shows an example graphical user interface (GUI) that may be presented on the display of a device that has been locked based on its designated user/owner being asleep consistent with present principles.

Now in reference to FIG. 3, assume as an example that an end-user's smart watch, electroencephalogram (EEG) headband, or other wearable device has a biometric sensor providing input to the wearable device and/or a smartphone with which the wearable device is Bluetooth paired. Either device may then determine, based on the input, that the end-user is asleep.

Determining that the user is asleep may therefore be performed a variety of different ways. For example, facial and action recognition may be used to respectively identify the user as the device owner and to identify the user as sleeping, both using input from a camera. Input from a microphone and sound recognition software may also be used to identify the user as sleeping based on audible breathing patterns indicated in the input and/or audible snoring being indicated in the input. Input from a motion sensor may indicate wearable device motion, and hence user motion, that is inconsistent with stasis while sleeping. Heart rate sensors and skin temperature sensors might also be used to determine the user is asleep (e.g., heart rates and patterns, and/or temperature amounts and fluctuations, matching predetermined heart rates/patterns and/or temperature amounts/fluctuations for sleeping). Electroencephalographs on a wearable headband may also be used to identify electrical activity in the wearer's brain and to match that activity to predetermined brain patterns to infer that the user is in a sleep state. Other implementations are encompassed as well.

Regardless of detection method used, responsive to the end-user being identified as asleep, one or both of the user's wearable device and smartphone may present the graphical user interface (GUI) 300 of FIG. 3 on that device's respective display. As shown in FIG. 3, the GUI 300 may establish a lock screen that includes a lock icon 310 to indicate that the respective device itself is locked. While the device is locked, other functions of the device may not be accessible to the end-user, such as ability to accept and make telephone calls, ability to text message, ability to access the Internet via a web browser or dedicated application ("app"), ability to access or launch software apps, etc.

FIG. 3 also shows that the GUI 300 may include a crescent moon and stars icon 320, providing a notification that the user/device owner is determined to be asleep. A text notification 330 may also be presented and indicate to any viewer of the GUI 300 that no biometric authentication is currently allowed to unlock the device.

In some example implementations, however, the device may still permit another method of authentication to the device to unlock the device while the user is asleep. As such, the GUI 300 may still include a numerical keypad 340 with number keys that the user may select in a particular sequence as part of a passcode to unlock the device notwithstanding the user being asleep. To provide enhanced digital security, this passcode might be a rotating passcode that changes every hour or every day and that follows a predetermined format. E.g., the passcode may be the current time of day expressed in hours and minutes, followed by the current day of the month, and concluding with a static pin as previously set at the device. Thus, this rotating dynamic passcode may permit another authorized user besides the device owner to still be able to unlock the device while the owner themselves is asleep, while at the same time enhancing digital security of the device by disabling biometric authentication methods that would be tied to the owner's own personal biometrics and hence would not be used while the owner is asleep.

Figure 4:
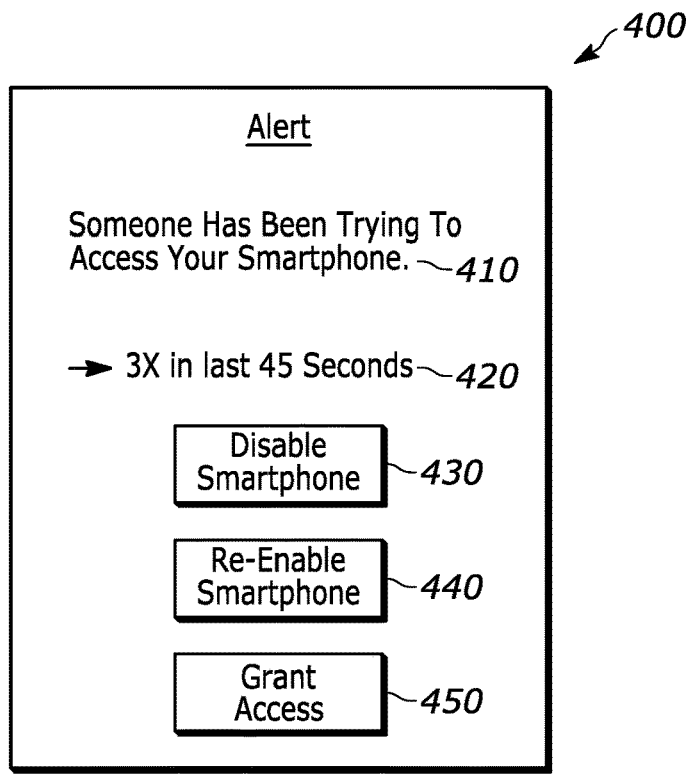
FIGS. 4 and 5 show example GUIs that may be presented based on unauthorized authentication attempts or device movement while the designated user/owner is asleep.

However, if an unauthorized user were in fact to attempt unauthorized unlocking of the smartphone while the smartphone's owner is asleep, possibly by taking the owner's finger and placing it on the smartphone's fingerprint sensor or holding the smartphone's camera up to the sleeping user's face for facial recognition authentication, the GUI 400 of FIG. 4 may be presented at the user's wearable device. In some specific examples, the GUI 400 may be presented at whatever wearable device is specifically determined to be currently worn by the user/owner (e.g., determined based on biometric input being received from that device's sensor, as also used to track the user's sleep).

The GUI 400 may therefore serve as a visual notification that someone is attempting unauthorized access to the smartphone. But also note that an audible alert may also be presented at the wearable device through the wearable device's speaker, with the audible alert using a computerized voice of a digital assistant to read aloud the text 410 presented on the GUI 400. Additionally or alternatively, the audible alert may be a non-verbal tone or melody or emergency alert signal. Also note that vibration alerts may also be presented at the wearable device, with the wearable device vibrating at high-intensity vibration using a vibrator within the wearable device to help wake the user (along with the audible alert(s) that might also help do so).

As shown in FIG. 4, the aforementioned text 410 may indicate that someone has been attempting to access the user's smartphone. As also shown, the text 410 may further indicate, via a dynamically increasing counter/timer 420, a number of times that authentication was attempted within a certain amount of time. The counter/timer 420 may therefore indicate a number of incorrect authentication attempts within an amount of time that has transpired since the first unauthorized authentication attempt was made for this particular instance.

The GUI 400 may also include selectors 430-450 for the user to direct touch or cursor input to one of them for selection. The selector 430 may be selectable to provide a command for the wearable device to remotely disable the smartphone so that it remains locked and cannot be subsequently unlocked for at least a threshold amount of time (e.g., ten minutes) and/or until the owner re-enables access. The owner may then ascertain the whereabouts of his/her smartphone and select selector 440 to reenable access to the smartphone (e.g., allow unlocking of the smartphone at the smartphone itself using biometric authentication and/or other types of authentication).

However, if the owner wishes to remotely unlock the smartphone from the wearable device itself rather than just reenabling authentication use at the smartphone to unlock the smartphone locally, the owner may select selector 450 to remotely command the smartphone to unlock its lock screen and render a home screen or app list, for example.

Figure 5:
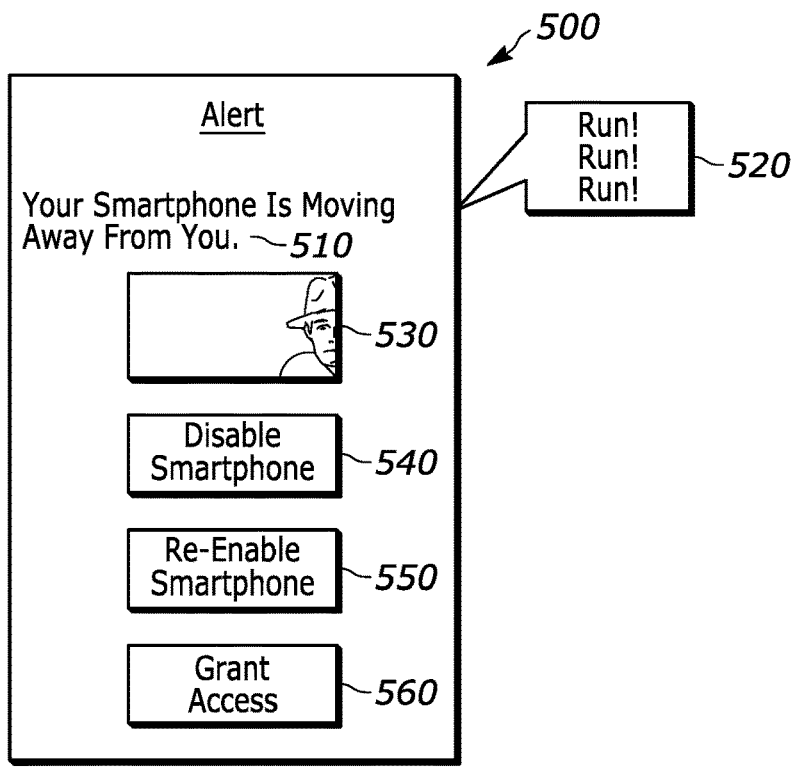

FIG. 5 shows another example GUI 500 that may be presented at the wearable device when one or both devices determine that the owner is asleep but the smartphone's motion sensors(s) still detect movement of the smartphone itself. The GUI 500 may therefore be presented since logically the sleeping owner wouldn't be moving the device and therefore this device movement might indicate device theft or other unauthorized control.

Thus, smartphone accelerometer and/or gyroscope input may be used to detect smartphone motion. Additionally or alternatively, GPS coordinates reported by the smartphone's GPS transceiver over time may indicate that the smartphone is changing locations while the user is asleep, indicating smartphone motion. In either case, responsive to smartphone movement being detected, the GUI 500 of FIG. 5 may be presented on the display of the user's wearable device. Again note that this visual alert may be presented in addition to or in lieu of vibration alerts. It may also be presented in addition to or in lieu of audible alerts reading the text 510 aloud and/or non-verbal tones similar to as set forth above. Further still, as shown via the speech bubble 520 of FIG. 5, an audible alert in the form of an audio live feed streamed from the smartphone's microphone may be presented at the wearable device's speakers so that the owner can hear audio proximate to the smartphone itself to help determine why the smartphone is moving. In the present instance, an apparent thief is exclaiming "Run! Run! Run!" as picked up by the smartphone's microphone.

As for the text 510 itself, it may indicate that the smartphone is moving away from the owner, as might be determined from the motion sensor input itself and/or based on GPS coordinates for the wearable device being compared to GPS coordinates from the smartphone to determine that one device is moving away from the other. The text 510 may be accompanied by a video live feed 530 as streamed from the smartphone's camera(s) so that the owner can see the current field of view of the camera itself to help determine why the smartphone is moving. In the present instance, the live feed 530 shows part of an apparent thief's face as captured by the smartphone camera.

As also shown in FIG. 5, the GUI 500 may include selectors 540, 550, and 560. Selector 540 may be selectable to command the smartphone similar to selection of the selector 430. Selector 550 may be selectable to command the smartphone similar to selection of the selector 440. Selector 560 may be selectable to command the smartphone similar to selection of the selector 450.

Figure 6:
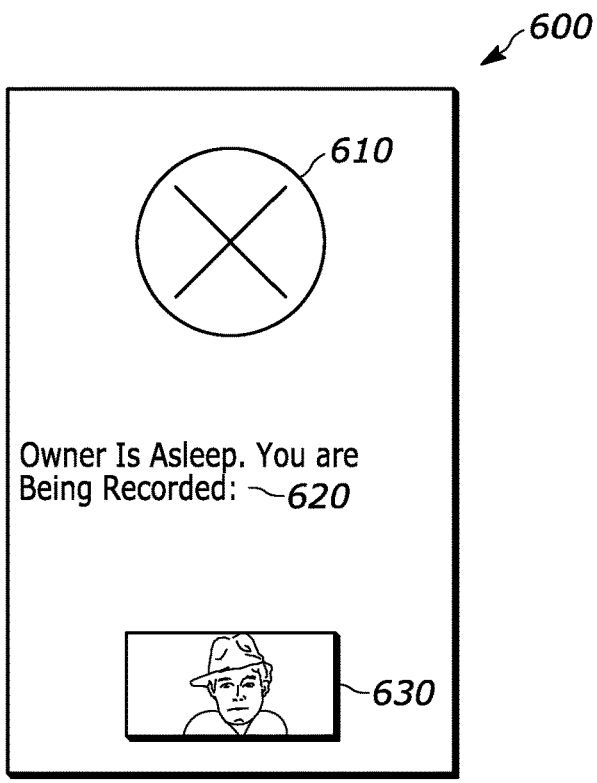
FIG. 6 shows an example GUI that may be presented on the display of the device at which unauthorized authentication is attempted or unauthorized movement detected.

Turning to FIG. 6, yet another example GUI 600 is shown. The GUI 600 may be presented on the display of the smartphone itself responsive to an unauthorized authentication attempt, detection of smartphone movement while the user is still asleep, or another trigger. The GUI 600 may include a graphical red "X" icon 610 (or other graphical object) surrounded by a circle to denote that an unauthorized action has been attempted at the smartphone. The GUI 600 may also include text 620 indicating that the smartphone's owner is asleep and that the third party is being recorded, e.g., audibly and visually. As such, the GUI 600 may also include a live feed 630 as captured by the smartphone's own forward-facing camera so that the third party is able to see themselves being recorded. Further note that both the audio and video streams from the smartphone may be recorded/ stored in server cloud storage, and/or livestreamed to and stored at the owner's wearable device itself.

Figure 7:
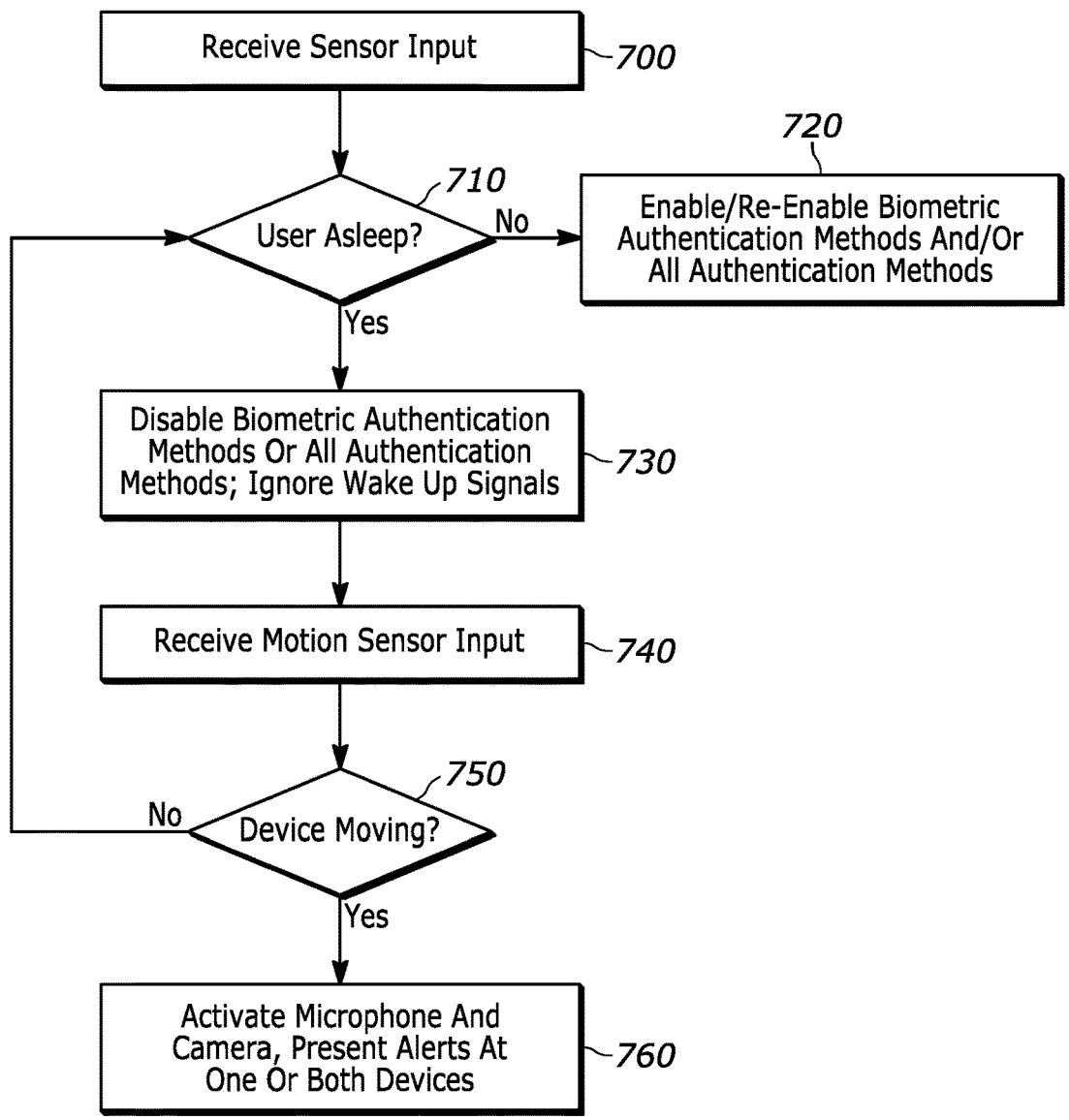
FIG. 7 illustrates example logic in example flow chart format that may be executed by an apparatus consistent with present principles.

Now Referring to FIG. 7, it shows example logic that may be executed by a processor assembly in one or more devices, such as in a wearable device and/or smartphone according to the example above, in any appropriate combination consistent with present principles. Thus, in certain examples all steps in the logic may be executed at a single client device to present notifications and to control locking/unlocking functionality of that device at that device alone. However, in other examples, various steps in the logic may be performed by one and/or the other of two client devices that are wirelessly communicating with each other as set forth above (e.g., with at least one of those devices having a biometric sensor for detecting the end-user being asleep). As yet another example, a remotely-located server routing communications between the two client devices may execute some or all of the logic steps. Further note that while the logic of FIG. 7 is shown in flow chart format, other suitable logic may also be used.

Beginning at block 700, the apparatus may receive input from one or more biometric sensors on a first device, with the biometric sensors sensing biometrics of an end-user (e.g., device owner). From block 700 the logic may then proceed to decision diamond 710 for the apparatus to determine, based on the input, whether the user is asleep. Any of the techniques disclosed above may be used to do so, as well as other methods of sleep tracking and/or detection.

A negative determination at diamond 710 may cause the logic to proceed to block 720 where, based on the user being in an awake state, the apparatus enables or re-enables biometric authentication methods and/or all authentication methods executable for device unlocking. However, an affirmative determination at diamond 710 may instead cause the logic to proceed to block 730.

At block 730, based on the determination that the user is asleep, the apparatus may disable at least a first type of authentication usable to unlock a second device (e.g., same device or different device). In some examples, for enhanced security, at block 730 the apparatus may disable all types of biometric authentication from being usable to unlock the second device, or even globally disable all types of authentication from being used for device unlocking. In terms of biometric types of authentication that might be disabled at block 730, example types include facial identification, fingerprint identification, and voice identification.

In some examples, from block 730 the logic might revert back to block 700 to receive additional biometric sensor input generated later in time and then determine, for example, that the user is now awake based on that additional biometric input. In such an instance, the logic might then proceed to block 720 to re-enable biometric authentication and/or other forms of authentication at the relevant device to unlock that device. And note here that unlocking the device may include unlocking a lock screen of the second device to access additional applications and features of the device beyond the lock screen itself.

However, in other non-limiting embodiments, the logic of FIG. 7 might instead proceed from block 730 to block 740. At block 740 the apparatus may, while the user is asleep, receive input from a motion sensor on the second device (such as an accelerometer, gyroscope, and/or GPS transceiver). The logic may then proceed to decision diamond 750 where the apparatus may determine based on the motion sensor input whether the second device is moving. Thus, based on the motion sensor input indicating movement of the second device, the logic may proceed to block 760 where the apparatus may activate a microphone on the second device and/or a camera on the second device to then livestream the microphone and/or camera input to the first device. For example, a smartphone camera and microphone feed may be transmitted from a smartphone to a wearable device according to the example of FIGS. 3-6.

Also note for completeness that should a negative determination be made at diamond 750, the logic might instead revert back to block 700 or diamond 710 and proceed again therefrom.

Also consistent with the logic of FIG. 7, note that in some examples the logic may additionally or alternatively proceed from block 730 to another step where the apparatus may, while the user is determined to still be asleep, identify a wake up signal to wake up the second device to a full power state from a device inactive state. The inactive state might be a sleep state in which system state data is saved in RAM that remains energized (e.g., even if the CPU and display do not remain energized). Additionally or alternatively, the inactive state may be a hibernation state in which system state data from RAM is saved to persistent storage of the device and the RAM is also deenergized in addition to the CPU, display, and/or other system components. In either case, based on the determination that the user is still asleep, the apparatus may decline to wake up the device from whatever inactive state it is in responsive to identification of the wake up signal (even though the apparatus might otherwise wake the device up responsive to the wake up signal if the user were determined to be awake). So as an example, if biometric sensors on a user's smart watch were used to detect the user as asleep, the user's Bluetooth-paired laptop computer may not be awoken from its inactive state even if a key on the laptop's keyboard were pressed or another action taken to otherwise awaken the laptop from its inactive state.

Figure 8:
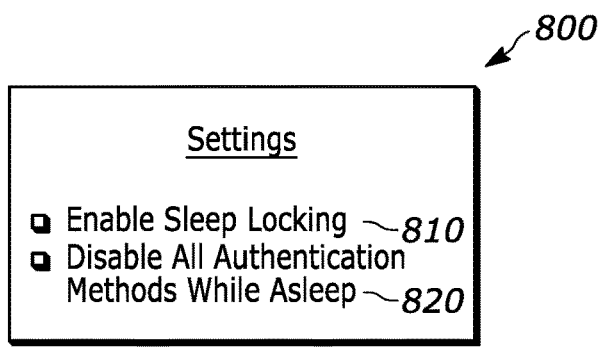
FIG. 8 shows an example settings GUI that may be presented on display to configure one or more settings of a device/processor assembly to operate consistent with present principles.

Continuing the detailed description in reference to FIG. 8, it shows an example GUI 800 that may be presented on the display of an apparatus (e.g., wearable biometric-sensing device and/or paired client device) to configure one or more settings of the device(s) to undertake present principles. The GUI 800 may be presented based on a user navigating a device or sleep monitoring app menu, for example. Also note that each of the example options described below may be selected via touch, cursor, or other input directed to the associated check box per this example.

As shown in FIG. 8, the GUI 800 may include a first option 810 that may be selectable a single time to set/configure the device to, for multiple future instances, monitor biometric input to determine whether a designated user is asleep and then take action as described herein. Thus, selection of the option 810 may set or enable the device/app to undertake the actions described above in reference to FIGS. 3-6 as well as to execute the logic of FIG. 7.

As also shown in FIG. 8, the GUI 800 may include an option 820. The option 820 may be selectable to set or configure the device to not only disable some or all forms of biometric authentication while the user is determined to be asleep (as might be set based on selection of the option 810), but to disable all forms of authentication from being used to unlock the relevant device while the user is asleep.

It may now be appreciated that present principles provide for an improved computer-based user interface that increases the functionality and security of the devices disclosed herein. The disclosed concepts are rooted in computer technology for computers to carry out their functions.

It is to be understood that whilst present principals have been described with reference to some example embodiments, these are not intended to be limiting, and that various alternative arrangements may be used to implement the subject matter claimed herein. Components included in one embodiment can be used in other embodiments in any appropriate combination. For example, any of the various components described herein and/or depicted in the Figures may be combined, interchanged or excluded from other embodiments.

What is claimed is:

1. An apparatus, comprising:
 a processor assembly; and
 storage accessible to the processor assembly and comprising instructions executable by the processor assembly to:
 receive first input from at least one sensor on a first device;
 determine, based on the first input, that a user is asleep;
 based on the determination, disable at least a first type of authentication usable to unlock a second device;
 while receiving an input that the user is asleep, receive second input from a motion sensor, the second input indicating movement of the second device; and
 based on the second input, activate one or more of: a microphone on the second device, a camera on the second device.

2. The apparatus of claim 1, comprising the second device.

3. The apparatus of claim 1, wherein the second device is different from the first device.

4. The apparatus of claim 1, comprising the first device.

5. A method, comprising:
 receiving first input from at least one sensor on a first device;
 determining, based on the first input, that a user is asleep;
 based on the determination, disabling at least a first type of authentication usable to unlock a second device;
 while receiving an input that the user is asleep, receiving second input, the second input received from a motion sensor on the second device, the second input indicating movement of the second device; and
 based on the second input, activating one or more of: a microphone on the second device, a camera on the second device.

6. An apparatus, comprising:
 at least one computer readable storage medium (CRSM) that is not a transitory signal, the at least one CRSM comprising instructions executable by a processor assembly to:
 receive first input from at least one sensor;
 determine, based on the first input, that a user is asleep;
 based on the determination, disable at least a first type of authentication executable by a device;
 while receiving an input that the user is asleep, receive second input from a motion sensor, the second input indicating movement of the device; and
 based on the second input, activate one or more of: a microphone on the device, a camera on the device.

7. The apparatus of claim 6, wherein the device is a first device, and wherein the instructions are executable to:
 based on the second input, activate both the microphone and the camera; and
 based on the activation, stream third input from the microphone and fourth input from the camera to a second device different from the first device.

8. The apparatus of claim 6, comprising the processor assembly.

9. The apparatus of claim 6, wherein the device is a first device, and wherein the instructions are executable to:
 based on the second input, activate the microphone on the first device; and
 based on the activation of the microphone, provide third input from the microphone to a second device different from the first device.

10. The apparatus of claim 6, wherein the device is a first device, and wherein the instructions are executable to:
 based on the second input, activate the camera on the first device; and
 based on the activation of the camera, provide third input from the camera to a second device different from the first device.

11. The apparatus of claim 1, wherein the instructions are executable to:
 based on the second input, activate the microphone on the second device.

12. The apparatus of claim 11, wherein the instructions are executable to:
 based on the activation of the microphone, provide third input from the microphone to another device different from the second device.

13. The apparatus of claim 1, wherein the instructions are executable to:
 based on the second input, activate the camera on the second device.

14. The apparatus of claim 13, wherein the instructions are executable to:
 based on the activation of the camera, provide third input from the camera to another device different from the second device.

15. The apparatus of claim 1, wherein the instructions are executable to:
 based on the second input, activate both the microphone and the camera; and
 based on the activation of the microphone and the camera, provide third input from the microphone and fourth input from the camera to another device different from the second device.

16. The method of claim 5, comprising:
based on the second input, activating the microphone on the second device.

17. The method of claim 16, comprising:
based on the activation of the microphone, streaming third input from the microphone to another device different from the second device.

18. The method of claim 5, comprising:
based on the second input, activating the camera on the second device.

19. The method of claim 18, comprising:
based on the activation of the camera, streaming third input from the camera to another device different from the second device.

20. The method of claim 5, comprising:
based on the second input, activating both the microphone and the camera; and
based on the activation of the microphone and the camera, providing third input from the microphone and fourth input from the camera to another device different from the second device.

* * * * *